[54] 17-CYCLOBUTYLMETHYL-3-HYDROXY-8β-METHYL-6-METHYLENE-MORPHINANE METHANESULFONATE

[75] Inventors: Michael P. Kotick; Joseph O. Polazzi, both of Elkhart, Ind.

[73] Assignee: Miles Laboratories, Inc., Elkhart, Ind.

[21] Appl. No.: 230,726

[22] Filed: Feb. 2, 1981

[51] Int. Cl.³ .................. C07D 221/28; A61K 31/485
[52] U.S. Cl. ...................................... 546/74; 424/260
[58] Field of Search .......................................... 546/74

[56] References Cited

U.S. PATENT DOCUMENTS 1,892,019  12/1932  Stoll et al. ............................. 546/44
4,259,329   3/1981  Kotick et al. ...................... 424/260

Primary Examiner—Glennon H. Hollrah
Assistant Examiner—Diana G. Rivers
Attorney, Agent, or Firm—Jerome L. Jeffers

[57] ABSTRACT

Disclosed is the title compound which has been found to be significantly more water soluble than other acid addition salts of the morphinane nucleus.

1 Claim, No Drawings

17-CYCLOBUTYLMETHYL-3-HYDROXY-8β-METHYL-6-METHYLENE-MORPHINANE METHANESULFONATE

BACKGROUND OF THE INVENTION

Morphine is a well known narcotic analgesic having the structural formula:

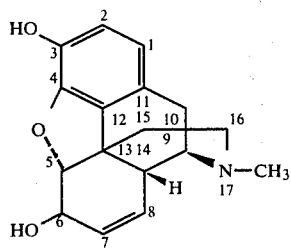

Morphine and its structurally related relatives are extremely effective for the relief of moderate to severe pain, however, these compounds are narcotic and most possess dependence-inducing liability and other side effects such as emesis, constipation, sweating, respiratory depression and myosis which make them less than ideal analgesics. A compound with the appropriate profile of analgesic (agonist) and narcotic antagonist activity has potential for treatment of moderate to severe pain without the liability of drug dependence or drug abuse. A compound having the desired profile, 17-cyclobutylmethyl-3-hydroxy-8β-methyl-6-methylene-morphinane, is disclosed in copending application Ser. No. 138,102, filed Apr. 21, 1980. This compound is well suited for use as a strong analgesic because of its agonist/antagonist profile.

Compounds of the type under consideration herein can be administered in the form of their free base, however, in many cases they are converted to their acid addition salts to increase their water solubility. Increased water solubility is desirable because it aids in the formulation of aqueous solutions for parenteral administration and assures a more rapid and uniform absorption or oral administration.

While the conversion of compounds of this type to their acid addition salts is known to have an effect on solubility, it cannot be predicted what effect a particular acid will have on the solubility of any specific compound.

SUMMARY OF THE INVENTION

The present invention is 17-cyclobutylmethyl-3-hydroxy-8β-methyl-6-methylene-morphinane methanesulfonate.

DESCRIPTION OF THE INVENTION

The method practicing the invention is illustrated by the following example:

EXAMPLE I

Preparation and determination of the solubility of various acid addition salts of 17-cyclobutylmethyl-3-hydroxy-8β-methyl-6-methylene-morphinan was accomplished as follows:

A. Methanesulfonate

To a stirred solution of the free base of the title compound, (1.01 g., 3 mmole), in absolute ether (60 ml.) was added methanesulfonic acid (0.214 ml., 317 mg., 3.3 mmole). The mixture was stirred at room temperature for 30 minutes and then the white crystals were collected, washed with ether and dried to give 915 mg. (70%) of the salt, m.p. 172°–188° C. Recrystallization of this material from boiling acetone ($\sim$100 ml.) gave 514 mg. (40%) of pure salt, m.p. 245°–250° C. Alternatively, the salt may be recrystallized from methanol-ethyl acetate.

Anal. Calcd. for $C_{23}H_{31}NO \cdot CH_3SO_3H$: C, 66.48; H, 8.14; N, 3.23. Found: C, 66.81; H, 8.37; N, 2.96.

B. Hydrochloride

The hydrochloride salt, m.p. 218°–220° C., was prepared in a similar fashion and obtained in pure form by recrystallization from methanol-ethyl acetate.

Anal. Calcd. for $C_{23}H_{31}NO \cdot HCl$: C, 73.87; H, 8.62; N, 3.75. Found: C, 73.73; H, 8.53; N, 3.73.

C. Hydrobromide

The hydrobromide salt, m.p. 210°–217° C., was obtained in crystalline form from ether.

Anal. Calcd. for $C_{23}H_{31}NO \cdot HBr$: C, 66.02; H, 7.71; N, 3.35. Found: C, 65.90; H, 7.57; N, 3.19.

Attempts to prepare the fumarate, tartrate, maleate, citrate, phosphate, acetate and sulfate salts were unsuccessful because these salts could not be obtained in analytically pure form. This was the case because they formed noncrystalline gels or mixtures of mon- and di-basic salts which could not be readily purified.

Solubility determinations were carried out by the addition of known portions of distilled water to a weighed sample of the salt until solution occurred with brief warming in a 50° C. water bath followed by shaking. Unexpectedly, the methanesulfonate salt was found to be soluble to the extent of 4% in distilled water. The analytically pure hydrochloride and hydrobromide salts were soluble to the extent of about 0.5%.

What is claimed is:

1. 17-cyclobutylmethyl-3-hydroxy-8β-methyl-6-methylene-morphinane methanesulfonate.

* * * * *